United States Patent [19]

Smits et al.

[11] Patent Number: 5,105,826

[45] Date of Patent: Apr. 21, 1992

[54] IMPLANTABLE DEFIBRILLATION ELECTRODE AND METHOD OF MANUFACTURE

[75] Inventors: Karel F. Smits, Oirsbeck; Antoine Camps, Wittem, both of Netherlands

[73] Assignee: Medtronic, Inc., Minneapolis, Minn.

[21] Appl. No.: 604,686

[22] Filed: Oct. 26, 1990

[51] Int. Cl.⁵ .............................................. A61N 1/05
[52] U.S. Cl. ............................ 128/784; 128/419 P; 128/642
[58] Field of Search .................. 128/783, 784, 419 P, 128/642

[56] References Cited

U.S. PATENT DOCUMENTS 4,026,303  5/1977  Babotai ........................... 128/419 P Primary Examiner—William E. Kamm
Assistant Examiner—Scott M. Getzow
Attorney, Agent, or Firm—Reed A. Duthler

[57] ABSTRACT

A defibrillation electrode fabricated by molding an elongated electrode core taking the form of two parallel segments each defining several sigmoidal curves, sliding a conductor coil over and along the electrode core, coupling the electrode coil to an elongated conductor, molding bridging members to connect the two segments of the core at spaced locations along the segments and molding a transition member to the electrode assembly at the junction of the electrode coil and the elongated conductor. The resulting electrode is particularly adapted for use as an epicardial defibrillation electrode, and displays flexibility within the plane defined by the electrode body as well as for twisting and other deformation to follow the changing surface of the heart during contractions.

10 Claims, 6 Drawing Sheets

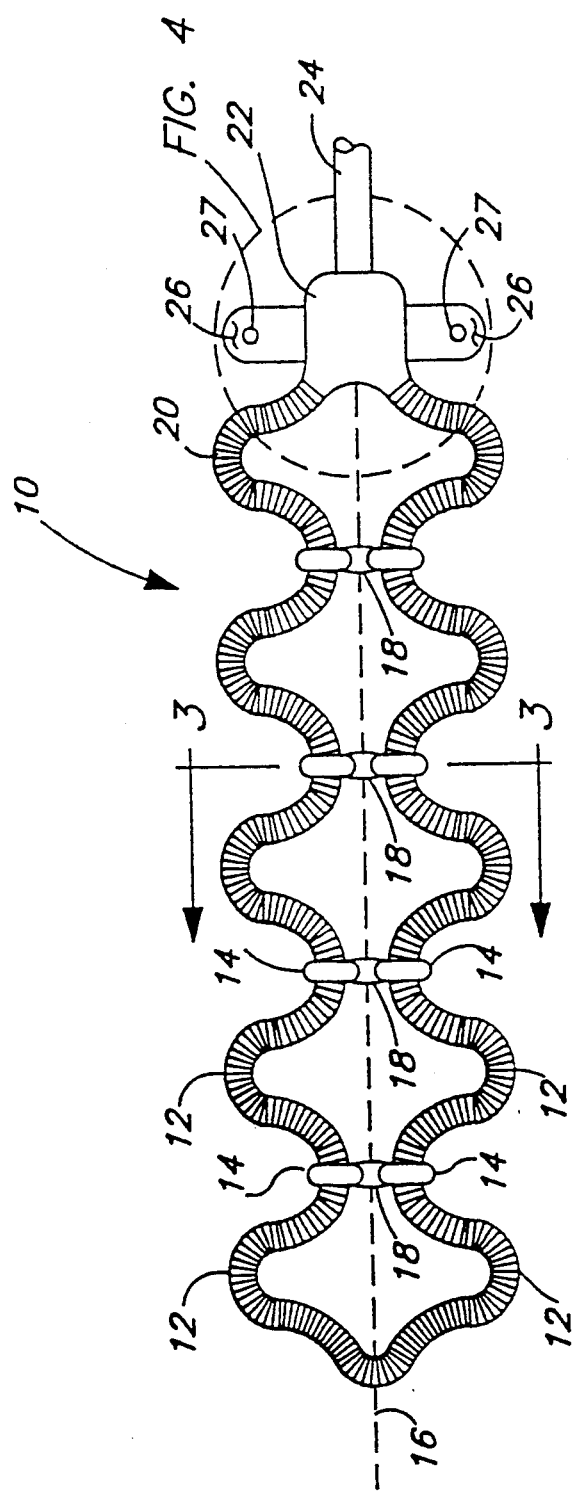
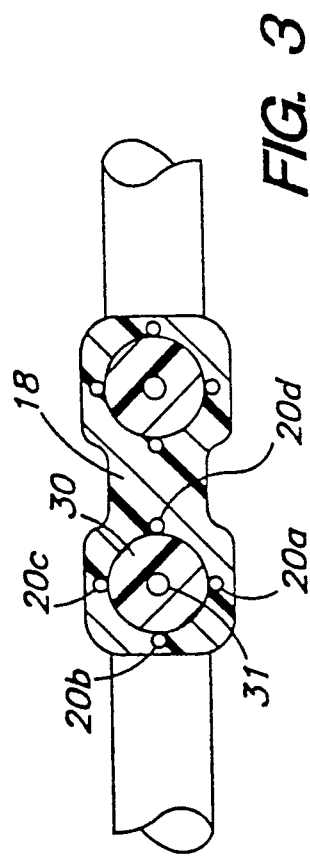

IMPLANTABLE DEFIBRILLATION ELECTRODE AND METHOD OF MANUFACTURE

BACKGROUND OF THE INVENTION

This invention relates generally to electrical medical leads and more particularly to epicardial defibrillation electrode leads.

Early epicardial defibrillation electrodes typically took the form of a wire mesh mounted in an insulative backing. Such electrodes are illustrated in design U.S. Pat. No. 274,262 issued to Heilman, U.S. Pat. No. 4,548,203 issued to Tacker et al and U.S. Pat. No. 4,827,932 issued to Ideker et al.

The above cited electrodes, while workable, do not exhibit the degree of flexibility that might be desired in conjunction with a large surface area defibrillation electrode. The surface of the heart undergoes a complex wringing motion characterized by longitudinal and circumferential dimensional changes and by angular shear deformation with each heartbeat. The heart, therefore, displays an actual change in surface area, with individual areas of the surface of the heart moving relative to one another during each contraction. Large surface area electrodes of fixed configuration cannot both maintain intimate contact with the surface of the heart and follow the surface of the heart as the heart beats.

A number of defibrillation electrodes do display increased flexibility and an ability to reshape themselves to conform to the changing surface of the heart. For example, the electrodes illustrated in U.S. Pat. No. 4,641,656 issued to Smits, FIGS. 6A, 7 and 10 display generally planar insulative electrode bodies with a plurality of individual conductive areas. These conductive areas may move relative to one another because of the provision of perforations extending through the lead body which allow relative movement of the electrodes within the plane defined by the lead body. This allows the individual electrode surfaces of the lead to remain adjacent heart tissue while it moves during contraction of the heart.

The form of the conductive surfaces employed in defibrillation electrodes has also changed in recent history. U.S. Pat. No. 4,817,634 issued to Holleman et al discloses a flexible electrode patch which employs an elongated electrode coil, rather than a wire mesh. The coil follows an elongated convoluted path along the electrode head and, in conjunction with the elasticity of the head provides some ability to conform to the heart as it changes shape during contractions. A similar electrode design, but lacking an insulative backing, is disclosed in U.S. Pat. No. 4,860,769 issued to Fogarty et al. In this lead, the electrode comprises a multifilar coil embedded in the surface of an elongated defibrillation electrode which displays a spiral configuration at its distal end. This spiral portion defines a generally planar insulative lead body with provision for allowing movement of individual conductive areas (turns of the electrode coil) relative to one another within the plane defined by the electrode body, and should be able to follow changes in configuration of the heart surface during contraction of the heart.

SUMMARY OF THE INVENTION

The present invention is also a defibrillation electrode lead which includes a generally planar, flexible insulative electrode body. In the present invention, the electrode body takes the form of an elongated electrode core formed of silicone rubber or other non-creeping polymer reinforced by a metal wire coil or coil electrode. The core takes the form of one or more sigmoidally curved segments. The curved segments are connected at proximal and/or distal ends and may be provided with bridging means connecting adjacent inwardly curved portions of the electrode core to one another. As such, the electrode body may be considered to display a series of perforations. The electrode surfaces mounted to the electrode body take the form of individual turns of an elongated monofilar or multifilar, conductive coil mounted around the cylindrical silicone rubber lead core. As in the Smits electrode described above, individual electrode surfaces (turns of the coil) may move with respect to one another within the plane defined by the electrode body.

The structure of the lead that is produced is particularly beneficial in that it is readily elastically extended in a longitudinal direction, is stretchable to some degree laterally, and may be twisted to follow virtually any three dimensional contour. The bridges connecting adjacent inwardly directed curves on the electrode body serve as convenient locations for sutures, staples or other mechanisms for anchoring the lead to the heart. In addition, leads according to the present invention may also be employed as subcutaneous electrodes, if desired.

The lead is particularly simple and convenient to manufacture, yet displays a high resistance to fatigue or fracture due to repeated flexing which is especially desirable in the context of an epicardial defibrillation electrode. The lead is formed by molding an elongated convoluted silicone rubber core displaying a curved configuration, sliding the electrode coil over the core, along its length, crimping both electrode coil ends to the elongated conductor, molding bridging members around the electrode coil and underlying electrode core in areas of adjacent inwardly directed curves, and molding the two open ends of the core and crimp assembly into a transition member, from which an elongated lead body extends. This process is substantially simplified as compared to the process for manufacturing the electrode described in the above-cited Fogarty application, and is believed to provide a substantial improvement in flexibility due to the fact that the electrode coil is not required to be embedded or otherwise molded into the surface of the lead body.

BRIEF DESCRIPTION OF THE DRAWINGS

FIG. 1 shows a top, plan view of the distal end of a defibrillation lead according to the present invention, including the electrode body and associated electrode coil.

FIG. 3 shows a cross section through the electrode body in the vicinity of the bridges connecting adjacent curved portions of the electrode core.

DETAILED DESCRIPTION OF THE INVENTION

Figure 2:
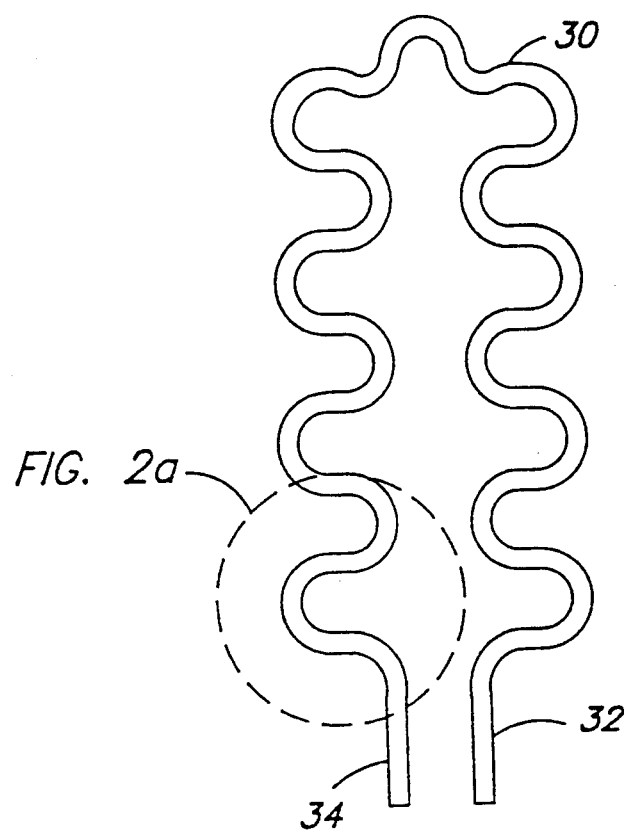
FIGS. 2 and 2a show the configuration of the elongated silicone rubber electrode core, prior to assembly of the lead.

FIG. 1 shows a top, plan view of the distal end of an electrode lead according to the present invention. As illustrated, the distal end of the electrode is provided with an electrode body 10, which takes the form of two generally parallel segments, each segment defining a plurality of sigmoidal curves. As illustrated, certain portions 12 of the electrode body have curves directed outwardly from the electrode body, whereas other portions 14 define curves which are directed inwardly toward the central axis 16 of the lead body. The lead body is constructed so that the inwardly directed curves 14 are located adjacent to one another and are connected by means of flexible insulative bridge members 18, which are molded to and around the elongated electrode coil 20, which extends the length of the electrode body. These bridge members 18 are convenient locations for sutures, staples, or other apparatus for attaching the lead to the surface of the heart. The sigmoidal curves allow for substantial elongation of the electrode body, twisting of the electrode body around its axis and bending around its axis in the plane of and perpendicular to the plane of the electrode body. The curves also allow for some expansion of the electrode body perpendicular to the axis.

At the proximal end of the electrode body is a transition member 22, which contains the junction between the electrode coil 20 and an elongated insulated conductor 24. This is illustrated in more detail in FIG. 4. Also provided on the transition member are suture tabs 26, which are typically provided with a Dacron mesh reinforcement for preventing tearing and holes 27 for passage of sutures.

In use, it is expected that two or more of these electrodes will be attached the surface of the heart by staples, surgical sutures or other means, and used to apply defibrillation pulses. The electrode may be applied perpendicular to or parallel to the axis of the heart. However, it is anticipated that in most cases two or more electrodes will be applied parallel to the axis of the heart, located primarily on the ventricles of the heart.

FIG. 2 shows an elongated silicone rubber electrode core 30, from which the electrode body assembly illustrated in FIG. 1 is fabricated. This electrode core is molded to display the curved sigmoidal configuration illustrated, and is provided with two open ends 32, 34. During assembly, a quadrifilar platinum coil, or a coil of other suitable material is passed along electrode core 30 until it extends along the coil from open end 32 to open end 34. The proximal ends of the multifilar coil are coupled to an elongated insulated conductor 24, and the assembly is placed into a mold. Bridges 18 and transition member 22 are then provided by a separate molding operation. Bridges 18 and transition member 22 may be fabricated of silicone rubber or other suitable material.

Figure 2A:
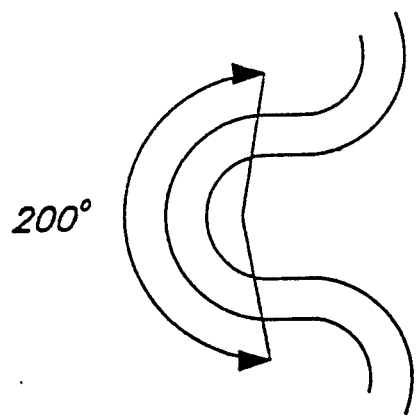

FIG. 2a illustrates that the curved radius of core 30 is smaller and the curve angle of the core is larger than for the electrode head assembly. This is because the electrode coil tends to straighten out the electrode core, after mounting, resulting in a curve angle as illustrated of approximately 180° after mounting, compared to approximately 200° prior to mounting. This also results in some elongation of the electrode head. The specific form of the core curvature depends upon the stiffness of the material chosen for the core, the stiffness of the electrode coil, and the final curve angle and curve radius desired for the electrode head assembly.

FIG. 3 illustrates a cross section through the lead in the area of one of the bridges 18. In this figure, it can be seen that the bridges are molded to the electrode core 30, and around the individual conductors 20A, 20B, 20C and 20D. The core wire 31 is also visible in this view. Core wire 31 serves to reinforce the core or to control its stiffness. It may take the form of a flexible metal or polymer wire or coil molded into core 30. If core wire 31 is manufactured of a conductive material, it may optionally be coupled to the electrode coil 20 at its proximal and distal ends. This serves to reduce the overall electrical resistance of the electrode head.

Figure 4:
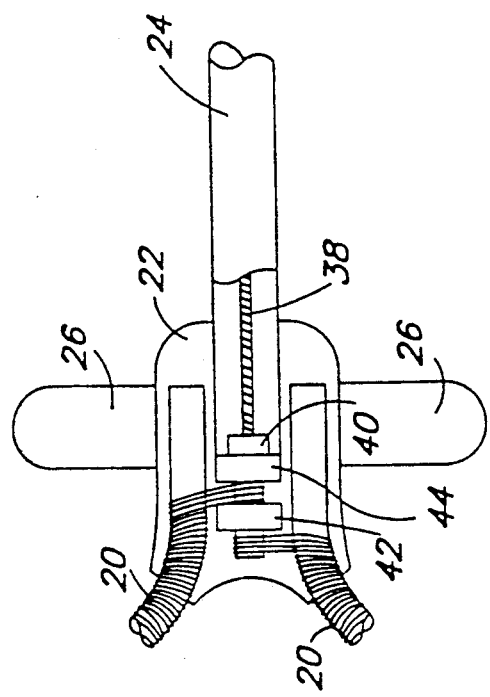
FIG. 4 shows the molded transition member, and the connection of the electrode coil to an elongated insulated conductor.

FIG. 4 shows a cutaway view in the vicinity of the transition member 22. In this view, it can be seen that the insulated conductor 24 includes an elongated conductor coil 38 crimped within a metal cylinder 40. The proximal ends of electrode coil 20 are wrapped around metal cylinder 40, and are crimped to metal cylinder 40 by means of crimping sleeves 42 and 44 which the hold the ends of the coil in contact with metal cylinder 40. These connections are made prior to the molding of transition member 22. Coupled to the proximal end of elongated insulated conductor 24 is a connector assembly not illustrated, which may be any commonly used medical electrical connector, and should correspond generally to those electrical connectors used in conjunction with prior art pacing and defibrillation electrodes. One appropriate connector is disclosed in U.S. Pat. No. 4,258,725, issued to O'Neill, incorporated herein by reference in its entirety.

Figure 5:
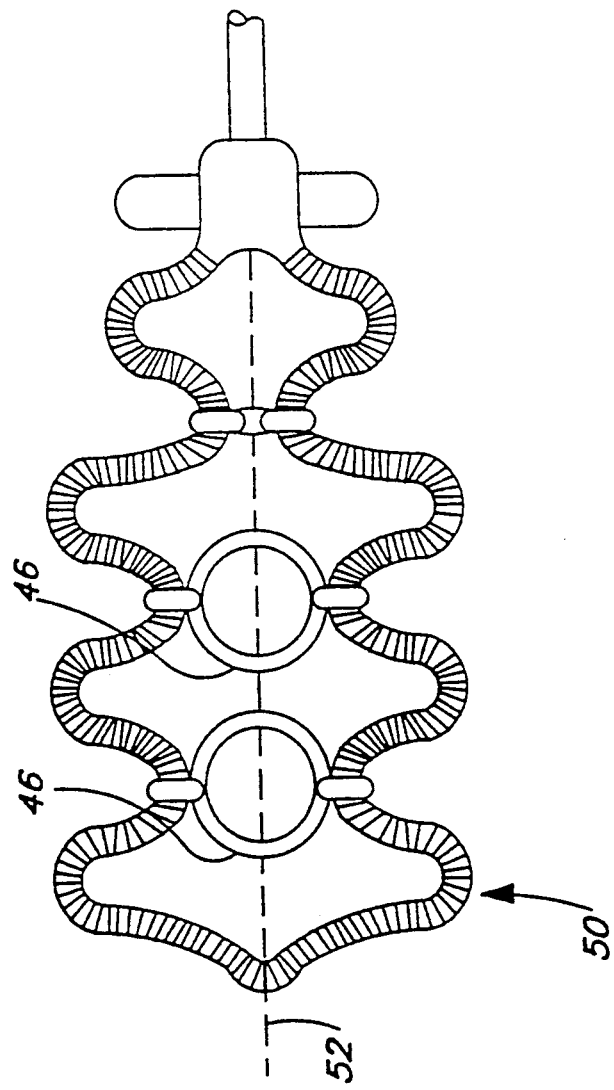
FIG. 5 shows an alternate embodiment of the electrode body of a lead according to the present invention.

FIG. 5 shows an alternate embodiment of the invention, which covers a greater surface area than the embodiment illustrated in FIG. 1 and displays a substantial increased ability to be stretched horizontally, perpendicular to the axis of the electrode body. In this case, the electrode structures correspond to those illustrated in FIG. 1, with the exception that two of the bridge members 46 take the form of silicone rubber loops, allowing for substantial lateral expansion of the electrode body 50 perpendicular to the axis 52 of the electrode body.

Figure 6B:
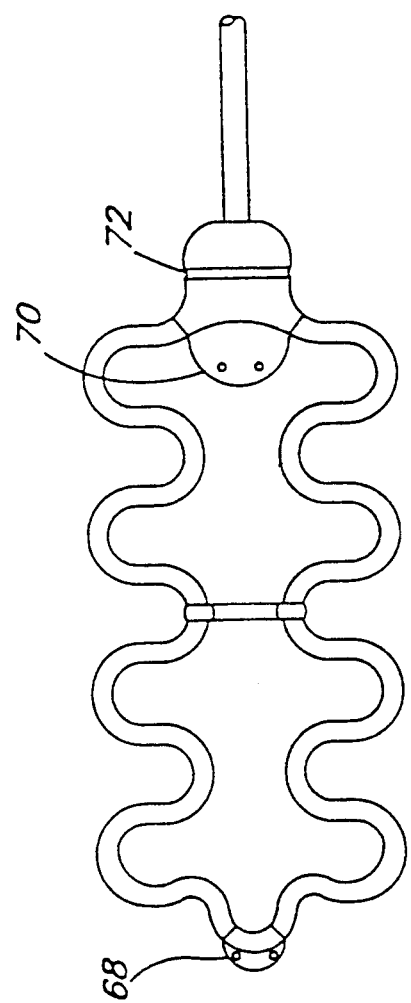
FIGS. 6a, b, c and d show additional alternate embodiments of the electrode body.
Figure 6A:
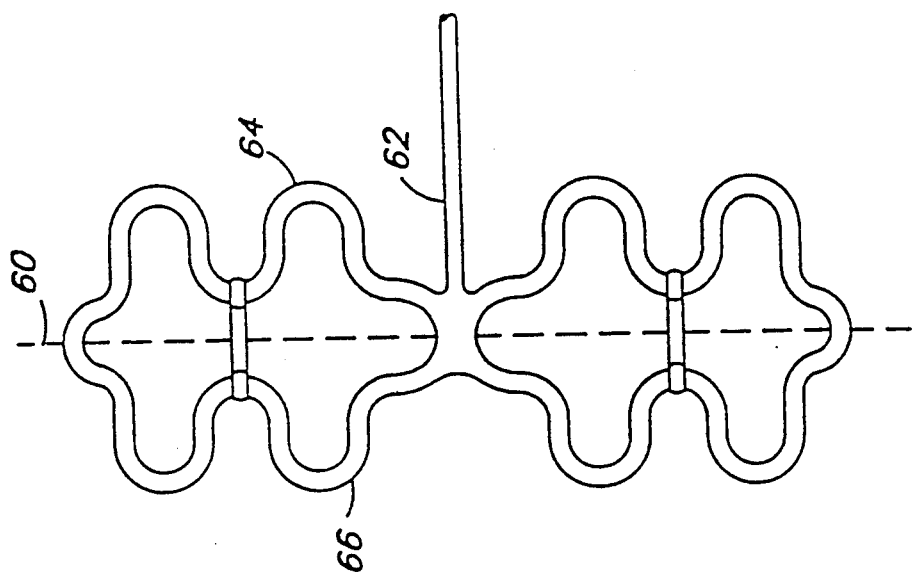

FIG. 6a shows an alternative embodiment of the electrode body of a lead according to the present invention, wherein the main axis 60 of the electrode body is perpendicular to the axis of the elongated conductor 62. The relationship of the sigmoidally curved segments 64 and 66, however, is similar to that illustrated in FIGS. 1-5, above.

FIG. 6b shows an additional alternative embodiment of an electrode body according to the present invention, with suture tabs 68 and 70 located at the distal and proximal ends of the electrode. A suture groove 72 is also illustrated as an alternative suturing means.

Figure 6C:
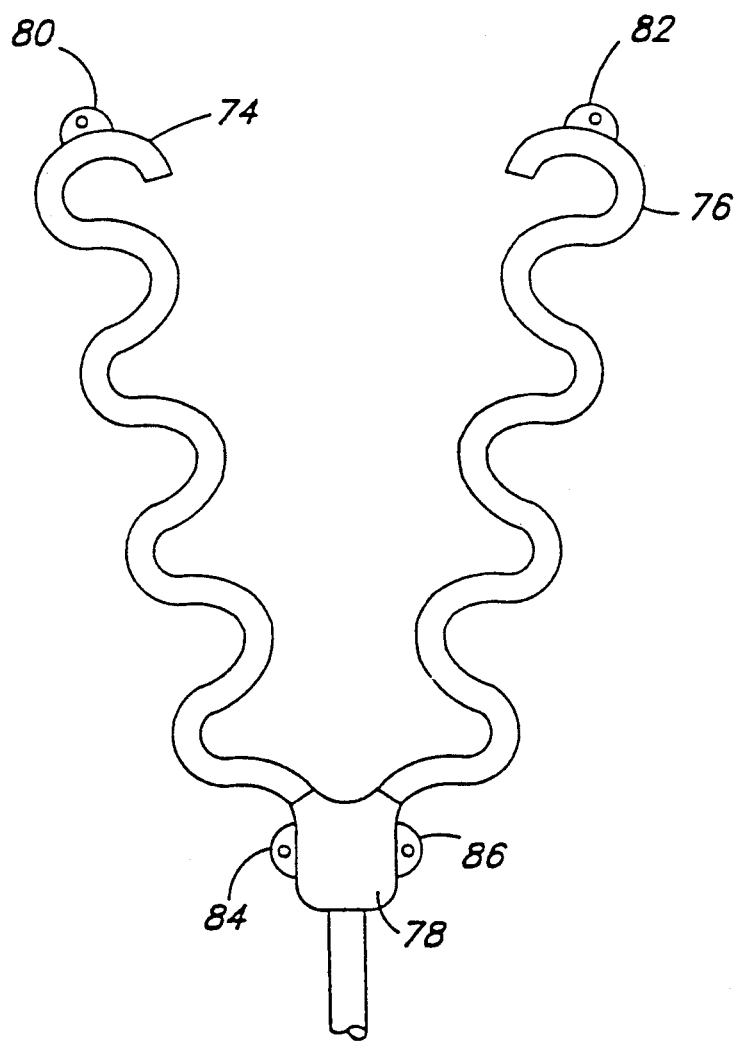

FIG. 6c illustrates yet another alternative embodiment of a lead body according to the present invention. In this embodiment, the distal ends of the signoidally curved segments 74 and 76 are not coupled to one another, and there are no bridging members connecting the adjacent portions of the curved segments, with the exception of the transition member 78. Suturing tabs 80, 82, 84 and 86 are provided at proximal and distal ends of the electrode head. This embodiment allows for placement of the electrode body between coronary arteries. The electrode is particularly valuable in the context of a patient who has had one or more coronary bypasses, as it avoids applying defibrillation energy adjacent the bypass sites.

Figure 6D:
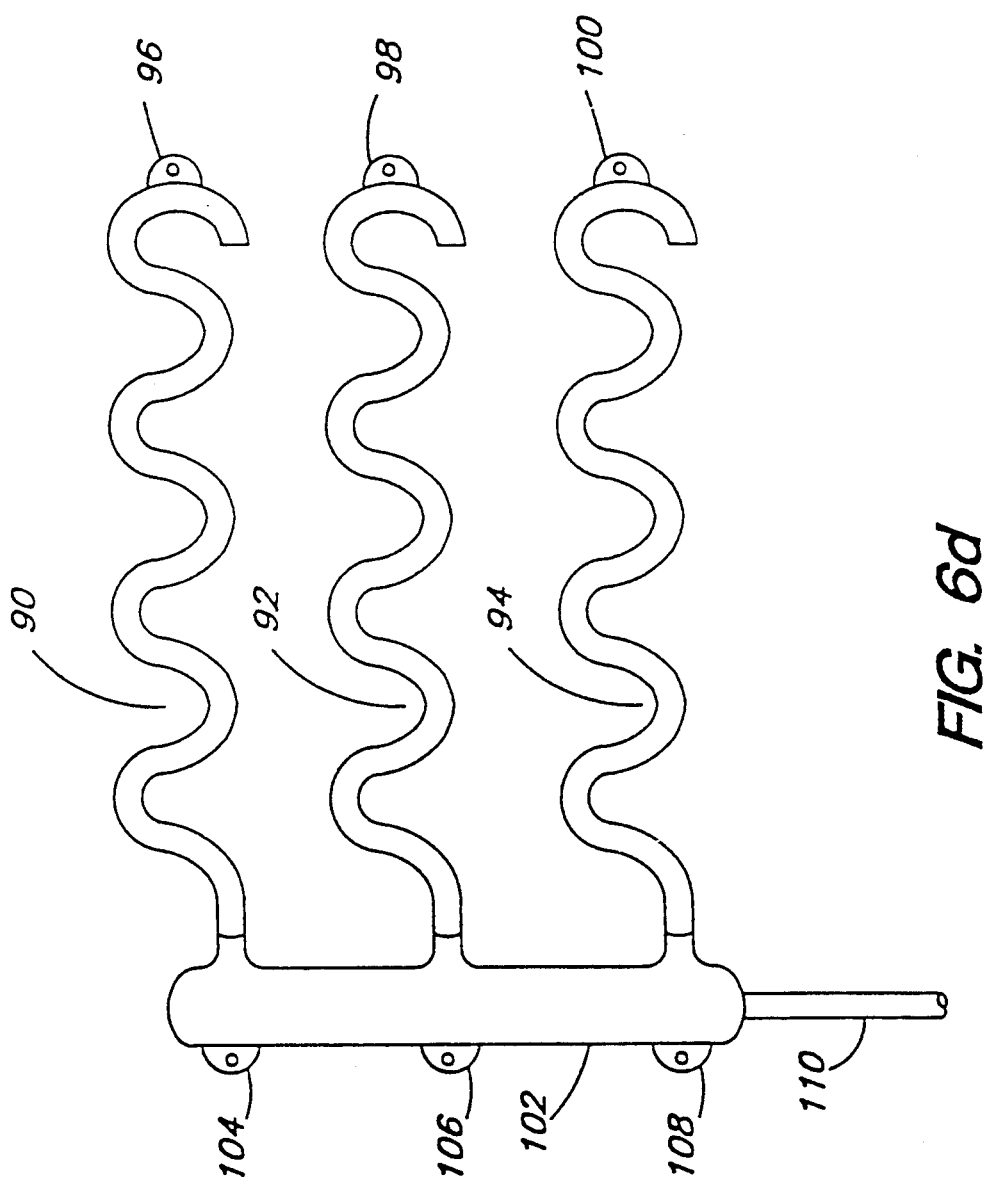

FIG. 6d illustrates an embodiment of the lead particularly adapted for subcutaneous implantation. The lead is provided with three sigmoidal segments 90, 92 and 94 extending from an elongated transition member 102. Each sigmoidal segment is provided with a suture tab, 96, 98, 100 The transition member 102 is similarly provided with suture tabs 104, 106 and 108. The electrode coils located on the sigmoidal segments are all coupled to a single insulated conductor 110. In use, the sigmoidal 90, 92 and 94 are placed subcutaneously between the ribs, so that the ribs do not interfere with delivery of defibrillation energy to the heart. The sigmoidal configuration of the electrode body segments allows for stretching and bending of the leads during respiration, as the rib cage expands and contracts.

The above embodiments all disclose electrode configurations employing two generally parallel segments of sigmoidal curves. However, it is believed that some benefit of the invention may also be obtained by employing individual electrodes, each taking the form of one segment defining a plurality of sigmoidal curves. The electrodes may be located adjacent one another to approximate the structure illustrated in FIG. 2, or might be located spaced from one another and connected at opposite polarities, depending upon the particular defibrillation pulse regime and electrode configuration desired. Although specifically adapted for use on the epicardium, the leads might also be employed as subcutaneous electrodes, if desired.

Further, although not illustrated above, one side of the electrode coil and the electrode body may be coated with silicone rubber, Tefzel ® polymer, parylene, polyurethane, PTFE or other insulative material to limit the exposed conductive area to only the portion of the electrode coil located adjacent the heart tissue.

As such, the above disclosed embodiments should be considered exemplary, rather than limiting with regard to the scope of the following claims. In conjunction with the above specification, we claim:

We claim:

1. An implantable defibrillation electrode lead comprising:
    an elongated insulated conductor coupled to an electrode body assembly, said electrode body assembly including a generally planar, flexible, insulative electrode body, said electrode body including an elongated flexible electrode core defining two generally parallel elongated segments, each of said elongated segments defining a plurality of sigmoidal curves located in the plane of said electrode body;
    an electrode coil mounted around said electrode core and extending along said electrode core, coupled to said elongated insulated conductor; and
    means for connecting adjacent portions of said first and second segments to one another, at locations spaced along said first and second elongated segments.

2. An implantable defibrillation electrode lead according to claim 1, wherein said electrode body defines a longitudinal axis and wherein each of said two generally parallel elongated segments are located on opposite sides of said electrode axis, wherein said sigmoidal curves defined by said parallel elongated segments of said electrode core are arranged such that inwardly curved portions of said segments are located adjacent one another, and wherein said connecting means connect said first and second segments to one another in the vicinity of adjacent ones of said inwardly directed curves.

3. An implantable defibrillation electrode lead according to claim 1 or claim 2 wherein said electrode coil comprises a multifilar coil.

4. An implantable defibrillation electrode lead according to claim 3 wherein said flexible electrode core comprises a molded, cylindrical silicone rubber core.

5. A method of fabrication of an implantable defibrillation electrode lead, comprising:
    molding an elongated flexible electrode core of an insulative, elastic plastic, said core defining two, generally parallel elongated segments, each of said elongated segments defining a plurality of coplanar sigmoidal curves;
    sliding an electrode coil over said electrode core along the length of said electrode core;
    connecting said electrode coil to an elongated, insulative conductor; and
    molding bridging members to said assembly of said core and said electrode coil, connecting said first and second segments to one another at locations spaced along said first and second elongated segments.

6. A method according to claim 5 wherein said method further comprises molding an insulative transition member to said electrode core and said electrode coil at the location at which said electrode coil is coupled to said elongated, insulated conductor.

7. An implantable defibrillation electrode lead, comprising:
    an elongated insulated conductor coupled to an electrode body assembly, said electrode body assembly including a generally planar, insulated electrode body, said electrode body including an elongated flexible electrode core defining a plurality of sigmoidal curves located in the plane of said electrode body;
    an electrode coil mounted around said electrode core and extending along said electrode core, coupled to said elongated insulated conductor; and
    means for mounting said electrode to a patient's heart.

8. An implantable defibrillation electrode lead according to claim 7 further comprising means for reinforcing said electrode body located Within said electrode core.

9. An implantable defibrillation electrode lead according to claim 8 whereby said reinforcing means comprises a metallic wire or coil, electrically connected to said electrode coil.

10. A method of manufacturing an implantable defibrillation electrode lead, comprising:
    molding a flexible, insulative electrode body including an elongated flexible electrode core defining a plurality of coplanar sigmoidal curves;
    sliding an electrode coil over said core, along the length of said core;
    coupling an elongated, insulated conductor to said electrode coil; and
    molding an insulative transition member over the junction of said electrode coil and said elongated coiled conductor.

* * * * *